(12) United States Patent
Deo et al.

(10) Patent No.: US 8,389,757 B2
(45) Date of Patent: Mar. 5, 2013

(54) PROCESS FOR PREPARING TERIFLUNOMIDE

(75) Inventors: Keshav Deo, Vadodara (IN); Samir Patel, Vadodara (IN); Snehal Dhol, Vadodara (IN); Sunil Sanghani, Vadodara (IN); Vishal Ray, Vadodara (IN)

(73) Assignee: Alembic Ltd., Gujarat (IN)

( * ) Notice: Subject to any disclaimer, the term of this patent is extended or adjusted under 35 U.S.C. 154(b) by 0 days.

(21) Appl. No.: 12/996,273

(22) PCT Filed: Jun. 3, 2009

(86) PCT No.: PCT/IB2009/052334
§ 371 (c)(1),
(2), (4) Date: Dec. 3, 2010

(87) PCT Pub. No.: WO2009/147624
PCT Pub. Date: Dec. 10, 2009

(65) Prior Publication Data
US 2011/0092727 A1   Apr. 21, 2011

(30) Foreign Application Priority Data
Jun. 5, 2008 (IN) .......................... 1215/MUM/2008

(51) Int. Cl.
*C07C 253/30* (2006.01)
(52) U.S. Cl. ....................................... 558/375
(58) Field of Classification Search .................. 558/375; 564/200
See application file for complete search history.

(56) References Cited

U.S. PATENT DOCUMENTS
6,331,555 B1   12/2001   Hirth et al.

FOREIGN PATENT DOCUMENTS
| WO | 99/54286 A2 | 10/1999 |
| WO | 00/56703 A1 | 9/2000 |
| WO | 99/54286 A2 | 9/2000 |
| WO | 02/34251 A1 | 5/2002 |
| WO | 2004/083165 A1 | 9/2004 |

OTHER PUBLICATIONS

"Derivative." Merriam-Webster Online Dictionary. 2010. Merriam-Webster Online. Accessed Apr. 20, 2010. <http://merriam-webster.com/dictionary/derivative>.*

* cited by examiner

*Primary Examiner* — Kristin Bianchi
(74) *Attorney, Agent, or Firm* — Sughrue Mion, PLLC

(57) ABSTRACT

The present invention relates to a process for preparing Teriflunomide of formula (I).

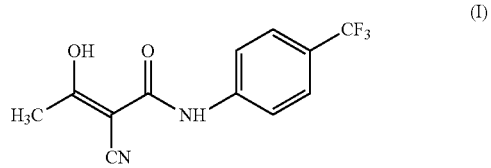

8 Claims, No Drawings

PROCESS FOR PREPARING TERIFLUNOMIDE

FIELD OF THE INVENTION

The present invention relates to a process for preparing Teriflunomide of formula (I).

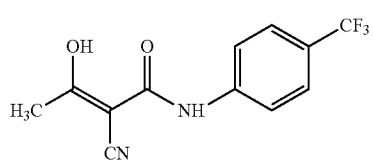

BACKGROUND OF THE INVENTION

The chemical name of Teriflunomide is 2-cyano-3-hydroxy-N-[4-(trifluoromethyl)phenyl]-2-butenamide and formula is $C_{12}H_9F_3N_2O_2$ and molecular weight is 270.207.

Teriflunomide is used as Immunosupressant. It acts as tyrosine kinase inhibitor. It is used in treatment of rheumatoid arthritis, autoimmune disease and multiple sclerosis.

Teriflunomide was first disclosed and claimed in U.S. Pat. No. 5,679,709 but this application does not mention the process of preparation.

U.S. Pat. No. 5,494,911 discloses a process for preparation of Teriflunomide in Example-4 as shown in given below scheme-I

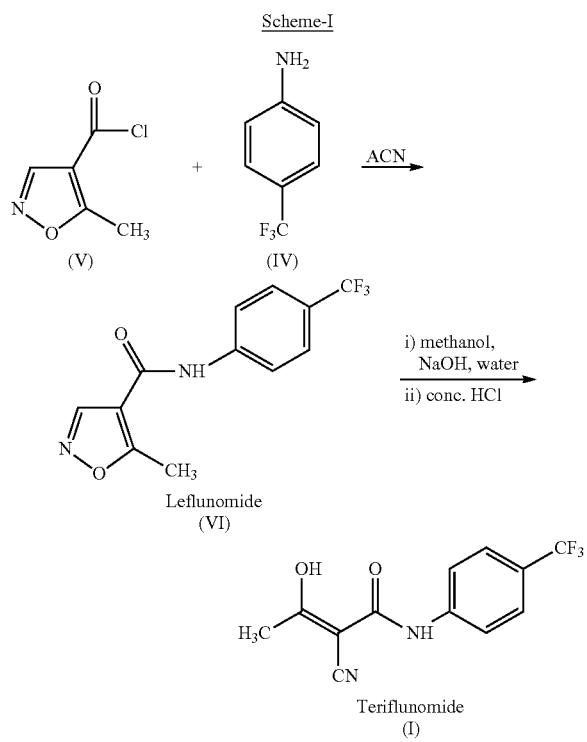

The process involves reacting 5-methylisoxazole-4-carbonyl chloride (V) with 4-trifluoromethylaniline (IV) in acetonitrile to give leflunomide (VI). The subsequent hydrolysis with aqueous sodium hydroxide solution in methanol gives Teriflunomide (I).

U.S. Pat. No. 5,990,141 discloses a process for preparation of Teriflunomide as shown in given below scheme-II.

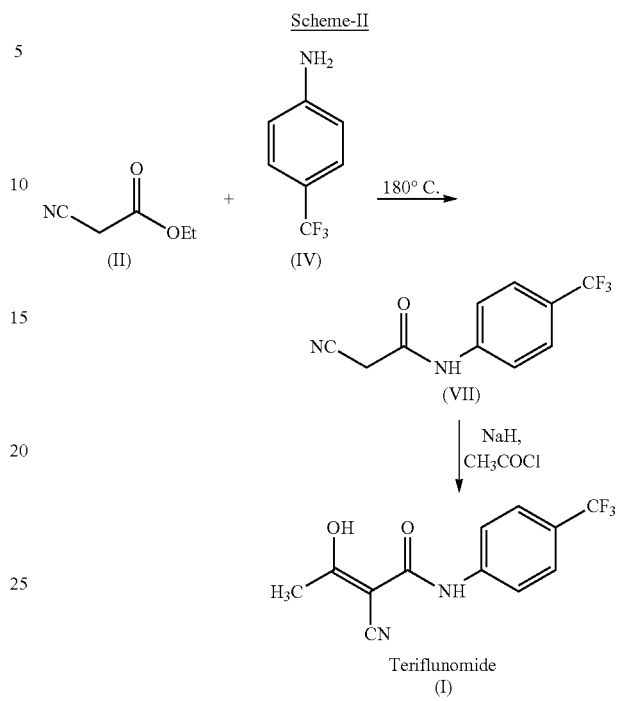

The process involves reacting 4-trifluoromethyl aniline (IV) with cyanoacetic acid ethyl ester (II) to give cyanoacet-(4-trifluoromethyl)-anilide (VII). This compound is further reacted first with sodium hydride in acetonitrile and then with acetylchloride in THF to give Teriflunomide (I).

U.S. Pat. No. 6,365,626 discloses a process for preparation of Teriflunomide in FIG. 19 which is as given in below scheme-III.

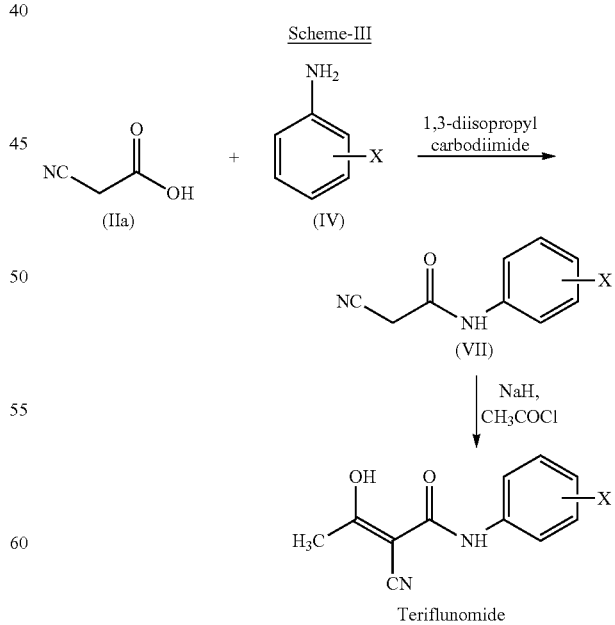

X = para CF₃

The process involves reacting 4-trifluoromethyl aniline (IV) with cyanoacetic acid (IIa) to give compound of formula (VII). This compound is further reacted first with sodium hydride and then with acetylchloride to give Teriflunomide (I)

All the above mentioned process requires chromatographic purification which in turn results in low yield.

It is therefore, a need to develop a process which not only overcomes the disadvantages of prior art but also be economical, operationally simple and industrially applicable.

Present inventors have directed their research work towards developing a process for the preparation of Teriflunomide which is devoid of the above mentioned disadvantages. The present inventor developed a novel process which not only reduce number of steps of reaction but is also feasible at commercial scale.

SUMMARY OF THE INVENTION

It is therefore an object of the present invention to provide a process for preparation of Teriflunomide.

Another object of the present invention is to provide a process for preparation of Teriflunomide which is simple and easy to handle at an industrial scale.

Accordingly, present invention provides a process for preparation of Teriflunomide (I)

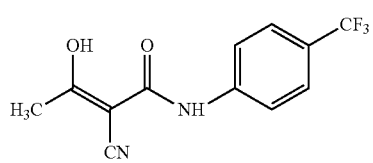
(I)

comprising steps of:
(i) reacting ethyl cyanoacetate (II)

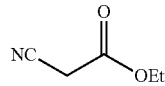
(II)

with an acetylating agent in the presence of a base optionally in the presence of a solvent to obtain Ethyl-2-cyano-3-hydroxy-but-2-enoate (III)

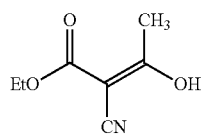
(III)

(ii) reacting Ethyl-2-cyano-3-hydroxy-but-2-enoate (III) with 4-trifluoromethyl aniline (IV)

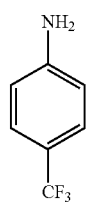
(IV)

optionally in the presence of a solvent to obtain Teriflunomide (I).

DETAILED DESCRIPTION OF THE INVENTION

Present invention provides a process for preparation of Teriflunomide (I)

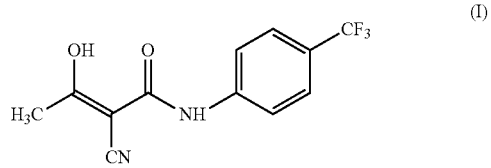 [SMILES: C/C(O)=C(\C#N)C(=O)Nc1ccc(C(F)(F)F)cc1]
(I)

comprising steps of:
(i) reacting ethyl cyanoacetate (II)

(II)

with an acetylating agent in the presence of a base and optionally in the presence of a solvent to give Ethyl-2-cyano-3-hydroxy-but-2-enoate (III)

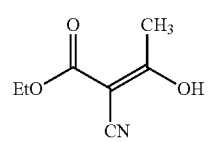
(III)

(ii) reacting Ethyl-2-cyano-3-hydroxy-but-2-enoate (III) with 4-trifluoromethyl aniline (IV)

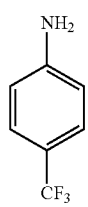
(IV)

optionally in the presence of a solvent to give Teriflunomide (I).

The present invention provides a process for preparation of Teriflunomide. Ethyl cyanoacetate is reacted with an acetylating agent such as acetic anhydride or acetyl chloride in the presence of a base and optionally in the presence of a solvent at room temperature. The base is selected from a group of organic base and inorganic base. Inorganic base is selected from alkali carbonate and bicarbonate, alkaline earth metal carbonate and bicarbonates, alkoxides and hydrides. The example of inorganic base includes but not limited to $NaHCO_3$, $KHCO_3$, $LiHCO_3$, $Na_2CO_3$, $K_2CO_3$, $Li_2CO_3$, $CaCO_3$, $MgCO_3$, sodium hydride, potassium tert butoxide, sodium tert butoxide and the like or mixtures thereof. Organic base is selected from pyridine and its derivative, piperidine, nitrogen containing base. The example of organic base includes but not limited to pyridine, piperidine, dimethyl amino pyridine, picolines, diisopropyl ethyl amine, triethyl amine and the like or mixtures thereof. The solvent is selected from DMF, acetonitrile, DMSO, Dimethylacetamide (DMAc), dichloromethane, dichloroethane, chloroform, carbon tetrachloride, toluene, xylene, nitrobenzene, acetone, methyl ethyl ketone and the like or mixtures thereof. The reaction mixture is quenched in water and extracted two to three times with organic solvent such as chlorinated solvent. The combined organic layer is washed with saturated sodium carbonate solution. The aqueous layer (carbonate layer) is separated and acidified with 50% HCl solution and extracted with organic solvent. Combined organic layer is washed with brine solution (100 ml), dried over sodium sulfate and concentrated to give Ethyl-2-cyano-3-hydroxy-but-2-enoate (III).

Ethyl-2-cyano-3-hydroxy-but-2-enoate (III) obtained in above step is heated with 4-trifluoromethyl aniline(IV) optionally in the presence of a solvent at elevated temperature from about 100° C. to about 180° C. The solvent is selected from a group comprising aliphatic hydrocarbon, cyclic hydrocarbon, and aromatic hydrocarbon. The examples of solvent includes but not limited to xylene, toluene, benzene, chlorobenzene diphenyl ether, cyclohexanone, isopropyl ether, DMSO, DMF, water and the like or mixtures thereof. After completion of the reaction, the reaction mixture is cooled at room temperature. Separated solid is filtered, washed with a solvent and suck dried. It may be the same solvent of reaction mixture or other solvent in which teriflunomide has less solubility. The compound is dried at about 40° C. to about 70° C. under vacuum to give the Teriflunomide (I).

The synthetic reaction scheme of the present invention is as shown below in scheme-IV

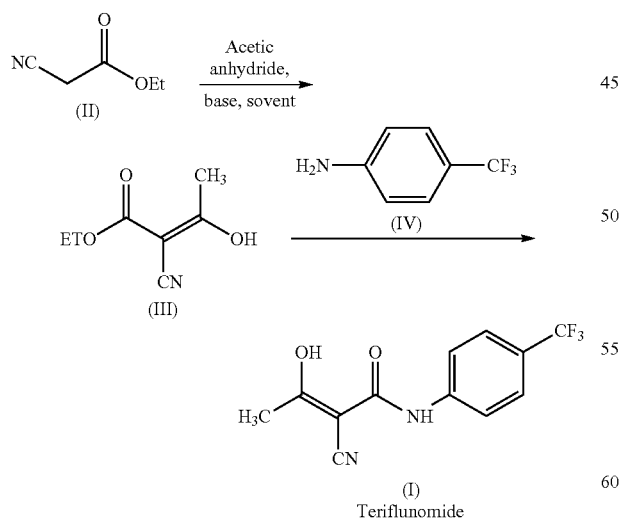

The following examples illustrate the invention further. It should be understood, however, that the invention is not confined to the specific limitations set forth in the individual examples but rather to the scope of the appended claims.

Example-1

Preparation of Ethyl-2-cyano-3-hydroxy-but-2-enoate (III)

Potassium carbonate (73.3 g) was added to the well stirred solution of Ethylcyanoacetate (50 g) in Dimethylformamide (250 ml) and stirred for 15 minute at ambient temperature. Acetic anhydride (90.25 g) was added drop wise to the above well stirred solution during 2 to 3 hours at ambient temperature. Reaction mixture was stirred at ambient temperature for 15 to 20 hours. Reaction mixture was diluted with water (500 ml) and extracted with dichloromethane (3×100 ml). Combined organic layer was washed with saturated sodium carbonate solution (3×100 ml). Aqueous carbonate layer was separated and acidified with 50% HCl solution and extracted with dichloromethane (3×100 ml). Combined organic layer was washed with brine solution (100 ml), dried over sodium sulfate and evaporated to yield Ethyl 2-cyano-3-hydroxy-but-2-enoate (58 g).

Yield: 84.6%

Example-2

Preparation of Teriflunomide (I)

Ethyl 2-cyano-3-hydroxybut-2-enoate (III) (50 g) and 4-(trifluoromethyl) aniline (51.9 g) in xylene (1000 ml) was refluxed for 48 hours. The reaction mixture was allowed to cool at room temperature. Separated solid was filtered and washed with xylene (2×100 ml). Solid was dried under vacuum at 70° C. to yield (62 g) of Teriflunomide.

Yield: 71.0%

Purity: 99.4%

$^1$HNMR (DMSO, 300 MHz): δ 2.24 (s, 3H); 5.36 (bs, 1H); 7.65 (d, J=8.7 Hz, 2H); 7.76 (d, J=8.6 Hz, 2H); 10.89 (s, 1H) ppm.

$^{13}$CNMR (DMSO, 75 MHz): δ 23.5, 82.1, 118.3, 122.2, 126.5, 126.9, 142.1, 167.4, 187.8 ppm.

Mass: 269 (M$^+$−1).

IR: 3305, 2220, 1633, 1596, 1554, 1418, 1405, 1325, 1247, 1114, 1157, 1073, 971, 842, 684 cm$^{-1}$.

We claim

1. A process for preparation of Teriflunomide (I)

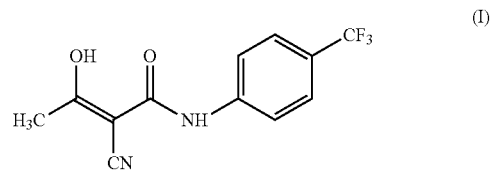 [SMILES: C/C(O)=C(\C#N)C(=O)Nc1ccc(C(F)(F)F)cc1]

comprising steps of:
reacting ethyl cyanoacetate (II)

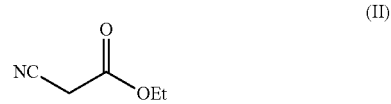

with an acetylating agent in the presence of a base and optionally in the presence of a solvent to obtain Ethyl-2-cyano-3-hydroxy-but-2-enoate (III)

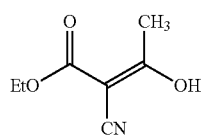 (III)

reacting Ethyl-2-cyano-3-hydroxy-but-2-enoate (III) with 4-trifluoromethyl aniline (IV)

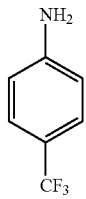 (IV)

optionally in the presence of solvent to give Teriflunomide (I).

2. The process as claimed in claim 1, wherein said acetylating agent is selected from acetic anhydride and acetyl chloride or mixture thereof.

3. The process as claimed in claim 1, wherein said base is selected from the group consisting of organic and inorganic base or mixture thereof.

4. The process as claimed in claim 3, wherein the organic base is selected from pyridine, piperidine, dimethyl amino pyridine, picolines, diisopropyl ethyl amine and triethyl amine or mixture thereof.

5. The process as claimed in claim 3, wherein the inorganic base is selected from the group comprising alkali carbonate and bicarbonate, alkaline earth metal carbonate and bicarbonates, alkoxides and hydrides or mixture thereof.

6. The process as claimed in claim 5, wherein alkali carbonate and bicarbonate, alkaline earth metal carbonate and bicarbonates, alkoxides, hydrides is selected from $NaHCO_3$, $KHCO_3$, $LiHCO_3$, $Na_2CO_3$, $K_2CO_3$, $Li_2CO_3$, $CaCO_3$, $MgCO_3$, sodium hydride, potassium tert butoxide and sodium tert butoxide or mixture thereof.

7. The process as claimed in claim 1, wherein the solvent for step (i) is selected from DMF, acetonitrile, DMSO, Dimethylacetamide, dichloromethane, dichloroethane, chloroform, carbon tetrachloride, toluene, xylene, nitrobenzene, acetone and methyl ethyl ketone or mixture thereof.

8. The process as claimed in claim 1, wherein the solvent for step (ii) is selected from xylene, toluene, benzene, chlorobenzene diphenyl ether, cyclohexanone, isopropyl ether, DMSO and DMF or mixture thereof.

* * * * *